(12) United States Patent
Miller

(10) Patent No.: US 8,093,313 B2
(45) Date of Patent: Jan. 10, 2012

(54) TISSUE SCAFFOLDING COMPOSITES

(75) Inventor: Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 254 days.

(21) Appl. No.: 12/606,771

(22) Filed: Oct. 27, 2009

(65) Prior Publication Data
US 2011/0097801 A1   Apr. 28, 2011

(51) Int. Cl.
*C08K 9/06* (2006.01)
*A61F 2/02* (2006.01)

(52) U.S. Cl. ...... 523/216; 523/113; 523/115; 623/23.58

(58) Field of Classification Search .................. 523/113, 523/115, 216; 623/23.58
See application file for complete search history.

(56) References Cited

U.S. PATENT DOCUMENTS

| | | | | |
|---|---|---|---|---|
| 5,977,204 | A * | 11/1999 | Boyan et al. | 523/113 |
| 7,935,143 | B2 * | 5/2011 | Wang | 623/1.42 |
| 2008/0064812 | A1 * | 3/2008 | Narayan et al. | 524/599 |
| 2010/0168798 | A1 * | 7/2010 | Clineff et al. | 606/279 |

FOREIGN PATENT DOCUMENTS
WO  WO 2007/017756   2/2007

OTHER PUBLICATIONS

K. M. Huh, "Synthesis and characterization of poly(ethylene glycol)/poly(L-lactic acid) alternating multiblock copolymers," *Polymer* 40 (1999), pp. 6147-6155; published by Elsevier Science Ltd.

Z. Hong et al., "Preparation and in vitro characterization of scaffolds of poly(L-lactic acid) containing bioactive glass ceramic nanoparticles," *Acta Biomaterialia* 4 (2008), pp. 1297-1306; published by Elsevier Ltd.

K. Rezwan et al., "Biodegradable and bioactive porous polymer/inorganic composite scaffolds for bone tissue engineering," *Biomaterials* 27 (2006), pp. 3413-3431; published by Elsevier Ltd.

A. Liu et al., "Surface modification of bioactive glass nanoparticles and the mechanical and biological properties of poly(L-lactide) composites," *Acta Biomaterialia* 4 (2008), pp. 1005-1015; published by Elsevier Ltd.

C. S. Proikakis et al., "Synthesis and Characterization of Low Molecular Weight Polylactic Acid," *Journal of Elastomers and Plastics* 34 (Jan. 2002), pp. 49-63; published by Sage Publications.

* cited by examiner

*Primary Examiner* — Tae H Yoon
(74) *Attorney, Agent, or Firm* — Foley & Lardner LLP

(57) ABSTRACT

A method for preparing a biocompatible polymeric composite includes modifying a first biocompatible polymer with a primer group to form a modified biocompatible polymer; blending the modified biocompatible polymer with a second biocompatible polymer and an inorganic material; allowing the primer group of the modified biocompatible polymer to react with the inorganic material to form a biocompatible polymeric composite. Such biocompatible polymeric composites may be formed into medical devices such as tissue growth scaffolds and bone growth scaffolds.

15 Claims, No Drawings

TISSUE SCAFFOLDING COMPOSITES

FIELD

The present technology is generally directed to tissue engineering composites, methods of making the composites, and methods of using the composites.

BACKGROUND

The following description is provided to assist the understanding of the reader. None of the information provided or references cited is admitted to be prior art.

Implantation of in vitro grown bone has been proposed as a method of healing broken, diseased, or malformed bones in patients. In vitro bone grown typically requires a porous scaffold to support the growing bone material. While the porous scaffolds should approximate the mechanical properties of bone as closely as possible, traditional porous scaffolds, particularly polymeric porous scaffolds, exhibit considerably lower tensile strength, compressive strength, and modulus than natural, cortical bone.

Improvements to the mechanical properties of polymeric porous scaffolds have been made via the incorporation of an inorganic substance, or phase, either as a mixture of the polymer and inorganic substance, or where the polymer has been bonded to the inorganic substance as a composite material. In such composites, stress is transferred from the polymer to the inorganic substance which has a higher strength than the polymer. One such inorganic substance is Bioglass®, however this material has presented numerous challenges. For example, hydrophilic Bioglass® particles are not compatible with hydrophobic polymers such as (poly)lactic acid. In the absence of a favorable interaction between the materials, they tend to phase separate, thereby compromising the integrity of composites formed of those materials. Where linkages between PLA and Bioglass® have been made, it is via a urethane chemistry and is not well-suited to medical applications due to concerns about the toxicity of the isocyanate chemistry used.

The polymer composites described herein provide for strong bonds between polymers and inorganic materials, thereby increasing the strength of the corresponding composites.

SUMMARY

In one aspect a method is provided including modifying a first biocompatible polymer with a primer group to form a modified biocompatible polymer; blending the modified biocompatible polymer with a second biocompatible polymer and an inorganic material; and allowing the primer group of the modified biocompatible polymer to react with the inorganic material to form a biocompatible polymeric composite. In some embodiments, the primer comprises a silane. For example, the silane may be a trialkoxysilane, a trihalosilane, or a triaminoalkylsilane. In some embodiments, a molecular weight of the first biocompatible polymer is less than a molecular weight of the second biocompatible polymer.

In some embodiments, the biocompatible polymers are individually a polyglycolic acid, polylactic acid, polyhydroxyalkanoate, polycaprolactone, poly(lactide-co-glycolide), polycarbonate, polyamide, polyanhydride, polyamino acids, polyorthoester, polyacetate, polycyanoacrylate, degradable polyurethane, degradable polyester, or a co-polymer or blend of such biocompatible polymers. In other embodiments, the biocompatible polymers are individually polylactic acid, polyglycolic acid, poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly (3-hydroxyheptanoate, poly(3-hydroxyoctanoate, poly(3-hydroxynonanoate), poly(3-hydroxytridecanoate), poly(3-hydroxytetradecanoate), poly(3-hydroxypentadecanoate), poly (3-hydroxyhexadecanoate), poly(3-hydroxyheptadecanoate), poly(3-hydroxyoctadecanoate), or a co-polymer or blend of such biocompatible polymers.

In some embodiments, the inorganic material is a glass or a ceramic material. For example, a glass may be a composition of $SiO_2$, $Na_2O$, $CaO$ and $P_2O_5$, commercially known as Bioglass®.

In some embodiments, the allowing the primer group of the modified biocompatible polymer to react with the inorganic material comprises forming a covalent bond between the modified biocompatible polymer and the inorganic material.

According to another aspect, biocompatible polymeric composites are also provided. In some embodiments, medical devices may be prepared from the biocompatible polymer composites. In other embodiments, the medical devices are tissue or bone growth scaffold materials. In yet other embodiments, the biocompatible polymeric composites may be formed via molding, extruding, machining, shaping, or the like.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In general, "substituted" refers to a group, as defined below (e.g., an alkyl or aryl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls(oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched alkyl groups having from 1 to 20 carbon atoms or, in some embodiments, from 1 to 12, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. Where the term haloalkyl is used, the alkyl group is substituted with one or more halogen atoms.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, CH=CH(CH$_3$), CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl, or arene, groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, polyhydroxyalkanoates refers to linear polyesters of a general formula:

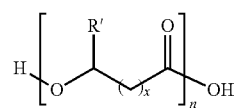

where R' is a substituted or unsubstituted alkyl, substituted or unsubstituted alkenyl, substituted or unsubstituted alkynyl, x is from about 1 to 20, and n is the repeat polymer unit as known to those of skill in the art. In some embodiments, n may be from 2 to 100,000, or more. Exemplary polyhydroxyalkanoates include, but are not limited to, poly lactic acid (PLA), poly glycolic acid (PGA), poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly(3-hydroxyheptanoate), poly(3-hydroxyoctanoate), poly(3-hydroxynonanoate), poly(3-hydroxytridecanoate), poly(3-hydroxytetradecanoate), poly(3-hydroxypentadecanoate), poly(3-hydroxyhexadecanoate), poly(3-hydroxyheptadecanoate), poly(3-hydroxyoctadecanoate), or a co-polymer or blend of any two or more such polymers As used herein, halogen can refer to F, Cl, Br, or I.

In one aspect, a biocompatible composite material is provided that may be formed into a tissue scaffold. The composite is made from an organic material and an inorganic material. The organic material may be a polymer, such as a bioactive polymer. Bioactive polymers are those polymers that are biocompatible and may be biodegradable. Inorganic materials include glasses and ceramics. The composites will exhibit good energy transfer from the organic portion to the inorganic portion, to provide a scaffold where stresses are readily distributed throughout the scaffold. Such a distribution of stresses throughout the scaffold provides for a strong material, avoiding localized stresses that can provide a site where failure of the scaffold may initiate. Such tissue scaffolds may be used for a variety of tissues, including, but not limited to, vasculature, cartilage, or bone, where the scaffolds approximate the material properties of native vasculature, cartilage, or bone.

As used herein, the term "tissue scaffold" is intended to refer to a structure upon which tissue may grow, and which is biocompatible. As used herein, "biocompatible" refers to a material that is compatible with a host in which the material is implanted.

As noted, the organic material used in preparing the biocompatible composite material for the tissue scaffold may be a polymer, such as a bioactive polymer. Bioactive polymers are those polymers that are biocompatible and may be biodegradable and/or bioabsorbable. As used herein, "bioabsorbable" refers to the absorption of the material by a host in which the material is implanted. As used herein, "biodegradable" refers to the ability of a material to be absorbed or eroded in the host in which the material is implanted either by chemical or physical means. In some embodiments, the polymers are bioabsorbable. The polymers may also be cross-linked, and the cross-link density may be adjusted to optimize the tensile and compressive properties of the polymer and polymer composites that may be prepared for use in the tissue scaffold.

Polymers that may be used include those based upon natural products such as PLA and PGA. Polymers such as PLA and PGA are generically known as polyhydroxyalkanoates. Other biocompatible polymers include materials such as polycaprolactone, poly(lactide-co-glycolide), polycarbonates, polyamides, polyanhydrides, polyamino acids, polyorthoesters, polyacetates, polycyanoacrylates, degradable polyurethanes, degradable polyesters, or co-polymers or blends of any two or more such polymers.

Polyhydroxyalkanoates that may be used in the tissue scaffolds include, but are not limited to, PLA, PGA, poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly(3-hydroxyheptanoate), poly(3-hydroxyoctanoate), poly(3-hydroxynonanoate), poly(3-hydroxytridecanoate), poly(3-hydroxytetradecanoate), poly(3-hydroxypentadecanoate), poly(3-hydroxyhexadecanoate), poly(3-hydroxyheptadecanoate), poly(3-hydroxyoctadecanoate), or a co-polymer or blend of any two or more such polymers.

In the biocompatible polymer composites, the organic material is bonded to the inorganic material. This is accomplished by modifying a low molecular weight, biocompatible polymer to include a primer group that is capable of reacting with the inorganic material. When the inorganic material, capable of reacting with the modified biocompatible polymer, and the modified biocompatible polymer are combined (or added together), a reaction is capable of occurring to form covalent bonds between the inorganic material and the biocompatible polymer to form a biocompatible polymer composite material.

The exact molecular weight to be used for a given application involves a balancing of the bioabsorbability, or biodegradation, and the mechanical properties of the polymer. The bioabsorbability, or biodegradation, of a polymer is inversely related to the molecular weight. In other words, as the molecular weight increases, the bioabsorbability decreases, and as the molecular weight decreases, the bioabsorbability increases. However, the mechanical properties of polymers are predominantly directly related to the molecular weight, such that as the molecular weight increases, the stronger the polymer becomes. Therefore, there is a balancing between the bioabsorbability, or biodegradation of a polymer and the mechanical properties that are imparted to a device prepared from the polymer.

As used herein, references to relative molecular weights of materials as "low," "moderate," and "high," are typically understood by the ordinary person of skill in the art. However, to the extent specific definitions may be provided, the molecular weight of the materials may range from a few thousand to several hundred thousand, or more, in order to maximize the mechanical properties for applications such as bone scaffolds, or orthopedic implants. To the extent specific molecular weights are need to define the relative terms of low, moderate, and high, the following definitions will apply. "Low molecular weight" will generally refer to those materials having a molecular weight of less than 5,000 g/mol. This includes molecular weights of from about 100 to about 5,000 g/mol, from about 500 to about 5000 g/mol, from about 1,000 to about 5,000 g/mol, from about 500 to about 4,000 g/mol, from about 1,000 to about 4,000 g/mol, from about 500 to about 3,000 g/mol, from about 2,000 to about 3,000 g/mol, from about 500 to about 2,500 g/mol, and from about 1,000 to about 3,000 g/mol. "Moderate molecular weight" will generally refer to those materials having a molecular weight of from about 5,000 to about 50,000 g/mol. "High molecular weight" will generally refer to those materials having a molecular weight of greater than 50,000 g/mol, such as 100,000 or greater. This includes molecular weights of from about 50,000 to 2,000,000 g/mol, from about 50,000 to 1,000,000 g/mol, from about 50,000 to 500,000 g/mol, from about 100,000 to 2,000,000 g/mol, from about 100,000 to 1,000,000 g/mol, from about 100,000 to 500,000 g/mol, 200,000 to 2,000,000 g/mol, from about 200,000 to 1,000,000 g/mol, from about 200,000 to 500,000 g/mol, from about 300,000 to 2,000,000 g/mol, or from about 500,000 to 2,000,000 g/mol.

Primer groups for modification of low molecular weight, biocompatible polymers have a terminal group that is capable of binding to the inorganic material, or a group associated with the inorganic material. Such groups include alkenes, amines, halosilanes, carboxylates, phosphonates, and alkoxysilanes. As used herein an alkoxysilane is a group having at least one Si—O—C bond that may be subjected to hydrolysis. Such primer groups may be incorporated in the polymer by treating the polymer with an acid chloride, followed by quenching with an alkenyl alcohol such as propanol, butenol, pentenol, hexenol, and the like. These alkenes can be subsequently converted to carbosilanes by treatment with a silane such as trimethoxysilane, triethoxysilane, trifluorosilane, trichlorosilane, tri(aminoalkyl)silane where the alkyl is $C_1$-$C_8$, such as tri(aminomethyl)silane. The silane may be a free silane, as illustrated in Scheme 1, or the silane may be associated with the inorganic material, as discussed below and in Scheme 2. Alternatively, an acid group on the polymer may be directly reacted with an alkenol in the presence of a catalyst to convert the acid group to an alkenyl ester that may then be reacted with an alkoxysilane to form the polymer with an alkoxysilane primer. This process is illustrated by Scheme 1.

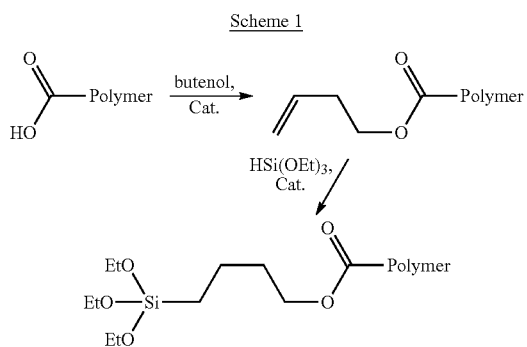

Scheme 1

In some embodiments, the terminal groups of the low molecular weight polymer may be modified with alkene, that may further be modified to an alkyl ester. In such embodiments, the low molecular weight polymer may then be mixed with the high molecular weight polymer before converting the alkenes to silyl esters. Such an approach may be utilized so that a minimum number of steps are performed on the low molecular weight polymer after the primer groups have been introduced.

Other primer groups are possible, as long as they are compatible with the solvents and chemicals used in this process. Application of primers to both end groups of a PLA may be accomplished by using a modified PLA synthesis. The use of low molecular weight polymers with primer groups allows for the end groups to be more numerous, and reduce the extent to which they are sterically shielded by the rest of the polymer chain in solution.

Because low molecular weight polymers lack the mechanical properties of high molecular weight polymers, low molecular weight polymer having a primer group may be blended, or diluted, with an unmodified high molecular weight polymer. Therefore in some embodiments, a first polymer (i.e. low or moderate molecular weight polymer) having a primer group may be blended, or diluted with a second polymer (i.e. a moderate or high molecular weight polymer) that is unmodified. Thus, the low, or lower, molecular weight polymer will be capable of binding with an inorganic material, while the high, or higher, molecular weight polymer will impart mechanical properties. Blending may be done prior to, or after, modification of the low molecular weight polymer with a primer, and the blending may be done in conjunction with blending of the polymer(s) with the inorganic material. For example, a low molecular weight polymer having a molecular weight of from about 100 to about 5,000 g/mol may be blended with a moderate molecular weight polymer having a molecular weight of from about 5,000 to about 50,000 g/mol. Alternatively, a low molecular weight polymer having a molecular weight of from about 100 to about 5,000 g/mol may be blended with a high molecular weight polymer having a molecular weight of from about 50,000 to about 2,000,000 g/mol. Alternatively, a moderate molecular weight polymer having a molecular weight of from about 5,000 to about 50,000 g/mol may be blended with a high molecular weight polymer having a molecular weight of from about 50,000 to about 2,000,000 g/mol. Alternatively, a low molecular weight polymer having a molecular weight of from about 100 to about 5,000 g/mol may be blended with a moderate molecular weight polymer having a molecular weight of from about 5,000 to about 50,000 g/mol, and a high molecular weight polymer having a molecular weight of from about 50,000 to about 2,000,000 g/mol.

Blending of the first and second polymers affords a manner in which one may exercise control over the density of primer groups in the material used to prepare the composites. Control over the composition of the final blend allows for just enough primer to be provided to react with the inorganic material, while limiting crosslinking of the polymer chains. The exact number of primer groups relative to total polymer mass will depend on the size of the inorganic material articles to be used, and the loading density.

The second polymer may be of the same or different polymer composition as the first polymer, differing only in the molecular weight of the respective polymers. For example, according to various embodiments, the first and second polymers may both be PLA, but with the second polymer having a higher molecular weight than the first. In some embodiments, the first polymer is a low molecular weight polymer and the second polymer is a moderate or high molecular weight polymer. In other embodiments, the first polymer is a moderate molecular weight polymer and the second polymer is a high molecular weight polymer.

According to some embodiments, the second polymer, or second biocompatible polymer, may be a PGA, PLA, PHA, polycaprolactone, poly(lactide-co-glycolide), polycarbonate, polyamide, polyanhydride, polyamino acid, polyorthoester, polyacetate, polycyanoacrylate, degradable polyurethane, degradable polyester, or a co-polymer or blend of any two or more such polymers. In some embodiments, the second biocompatible polymer is PLA, PGA, poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly(3-hydroxyheptanoate), poly(3-hydroxyoctanoate), poly(3-hydroxynonanoate), poly(3-hydroxytridecanoate), poly(3-hydroxytetradecanoate), poly(3-hydroxypentadecanoate), poly(3-hydroxyhexadecanoate), poly(3-hydroxyheptadecanoate), poly(3-hydroxyoctadecanoate), or a co-polymer or blend of any two or more such polymers. In other embodiments, the second biocompatible polymer is a unmodified PLA. In other embodiments, the second biocompatible polymer is unmodified PGA. In yet other embodiments, the second biocompatible polymer is an unmodified PLA-co-PGA material.

The inorganic material is a material that will assist in providing structural rigidity to the composites to be prepared and will react with the primer groups of the first polymer. The inorganic material may include, but is not limited to, glasses and ceramics. The inorganic material, like the organic portion is biodegradable, or bioabsorbable such that it is able to be cleared from the body. The inorganic material should not result in immune reactions upon implantation in a body, and it's degradation groups should be similarly tolerated. In some embodiments, the inorganic material is a microparticle, a nanoparticle, or a fiber. In some embodiments, the inorganic material has surface attached hydroxyl (—OH) groups that are capable of reaction with amine, halosilane, aminoalkylsilane and/or alkoxy silane groups that may be present as the primer group of the first polymer.

One such inorganic material is Bioglass®, a commercially available type of bioactive glass known by various tradenames such as 45S5 glass. Bioglass® is composed of $SiO_2$, $Na_2O$, CaO and $P_2O_5$. Bioglass® typically contains less than 60 mol % $SiO_2$, has high $Na_2O$ and CaO content, with a high $CaO/P_2O_5$ ratio that makes Bioglass® highly reactive to aqueous media, and bioactive. Additional inorganic materials include, but are not limited to, hydroxyapatite, calcium phosphates, and tricalcium phosphates.

In an alternative embodiment, the inorganic material may be modified with a primer group that is capable of reacting with the first polymer, or low molecular weight polymer in some embodiments. For example, the inorganic material may be reacted with an alkoxysilane such that the inorganic material will contain Si—H groups that may react with an alkenyl group on the first polymer, or low molecular weight polymer in some embodiments. By way of example only, reference for such is process is made to Scheme 2, where the catalyst is a hydrosilylation catalyst.

Scheme 2

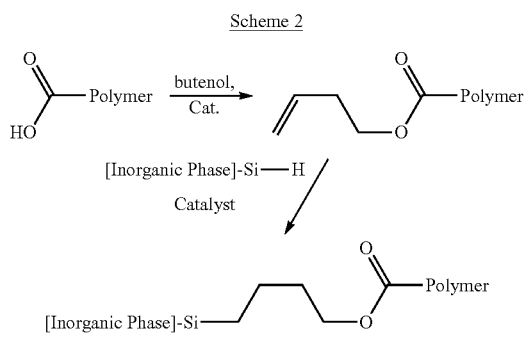

The reaction of a primer group on the first polymer with the inorganic material results in the formation of a biocompatible polymer composite. The biocompatible polymer composites may be processed into a wide variety of devices, including medical devices. Such medical devices may include a host of devices in which a bioabsorbable polymer is required such that after the device has performed its intended purpose, the material has been absorbed by the patient. Thus, in some embodiments, the medical devices are bioabsorbable or biodegradable. In particular, the medical devices can include those in which it is desirable that the device maintain structural integrity and respond to a variety of stresses before and/or during absorption of the device by the patient. Such medical devices include drug delivery systems (e.g., extended release systems), and tissue scaffolds such as bone growth scaffolds.

As described above, the composites contain covalent bonding between the inorganic material and the organic material. This allows for a distribution of stresses and energy transfer from one material to another within a structurally sound framework. The composite can be prepared by treating a blend of an inorganic material and a alkanoate silane-modified polymer with a small amount of acid to catalyze hydrolysis of the alkanoate silane bonds, or heated to accelerate the process. Alternatively, the reaction may be allowed to proceed slowly under uncatalyzed, ambient conditions. By way of understanding, the silyl esters (alkanoate groups on the silane) on the polymer end groups will be hydrolyzed to silyl alcohols, which will then condense with —OH groups on the surface of the inorganic material. Where the inorganic material is a glass, the —OH groups are also bonded to silicon atoms in the glass, and the covalent bonds between the glass and the polymer include Si—O—Si bonds.

Blends of the modified polymer and the inorganic materials may be prepared by dissolving the polymer in suitable solvent prior to addition of the inorganic material. Such suitable solvents include, but are not limited to, halogenated solvents, ketones, acetates, nitriles, arenes, alcohols, ethers, amides, and sulfonates, or a mixture of any two or more such solvents. For example, solvents may include chloroform, dichloromethane, carbontetrachloride, chloroethane, 1,2-dichloroethane, trichloroethane, acetone, acetonitrile, benzene, butyl acetate, butyl propionate, ethyl ether, isopropyl ether, β-butyrolactone, γ-butyrolactone, diethyl carbonate, diethylformamide, dimethyl carbonate, dimethyl succinate, dimethyl sulfoxide, dimethylformamide, ethyl acetate, ethylene glycol diacetate, methyl acetate, methyl ethyl ketone, methylisobutylketone, tetrahydrofuran, toluene, xylene, or a mixture of any two or more such solvents. According to some embodiments, the solvent is anhydrous, also some residual water may be present. In other embodiments, all adventitious water has been removed form the solvent. Another suitable solvent for polymers is supercritical carbon dioxide. Such solvent provides the benefit that it is readily made anhydrous, and that its removal can be accomplished via de-pressurization.

Blending of the inorganic material with the polymer material may be accomplished by suspending the inorganic material in a suitable solvent for the polymer. Such suspension may be assisted, in some embodiments, through sonication of the inorganic material and the solvent. In other embodiments, the polymer, inorganic material, and solvent are all mixed and sonicated together to suspend the inorganic material in the resultant mixture.

Once the composite material is prepared in the solvent, the solvent is removed. The solvent may be removed via evaporation at elevated temperature, under vacuum, or evaporation under ambient conditions. In embodiments where supercritical carbon dioxide is used as the solvent, to vessel used for preparation is de-pressurized to remove the carbon dioxide and the resultant composite. Where the solvent is a liquid medium, because the composite contains both polymer bound to the inorganic material and high molecular weight polymer unbound to the inorganic material, the composite is first precipitated from solution by using a precipitating solvent. According to some embodiments, precipitating solvents are miscible with the solvent used in the blending stage, but which cause precipitation of the polymer and composite materials in solution. Examples of precipitating solvents include water; alcohols such as methanol, ethanol, and isopropanol; and alkanes such as pentane, hexane, heptane, and octane.

The composite material that is then recovered after the removal of the solvent may be pressed, shaped, machined, extruded, or otherwise formed into the desired shape. Heat, i.e. sintering, may be used in the shape forming process. For example, the composite material may be heated above its glass transition temperature, with or without compression of the material, in a pre-determined shape, and then cooled such that the cooled composite maintains the desired shape.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Other embodiments are set forth in the following claims.

What is claimed is:

1. A method comprising:
   modifying a first biocompatible polymer with a primer group to form a modified biocompatible polymer;
   blending the modified biocompatible polymer with a second biocompatible polymer and an inorganic material; and
   allowing the primer group of the modified biocompatible polymer to react with the inorganic material to form a biocompatible polymeric composite;
   wherein the primer group comprises a silane.

2. The method of claim 1, wherein a molecular weight of the first biocompatible polymer is less than a molecular weight of the second biocompatible polymer.

3. The method of claim 1, wherein the first biocompatible polymer is a polyglycolic acid, polylactic acid, polyhydroxyalkanoate, polycaprolactone, poly(lactide-co-glycolide), polycarbonate, polyamide, polyanhydride, polyamino acids, polyorthoester, polyacetate, polycyanoacrylate, degradable polyurethane, degradable polyester, or a co-polymer or blend thereof.

4. The method of claim 1, wherein the first biocompatible polymer is polylactic acid, polyglycolic acid, poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly(3-hydroxyheptanoate), poly(3-hydroxyoctanoate), poly(3-hydroxynonanoate), poly(3-hydroxytridecanoate), poly(3-hydroxytetradecanoate), poly(3-hydroxypentadecanoate), poly(3-hydroxyhexadecanoate), poly(3-hydroxyheptadecanoate), poly(3-hydroxyoctadecanoate), or a co-polymer or blend thereof.

5. The method of claim 1, wherein the second biocompatible polymer is a polyglycolic acid, polylactic acid, polyhydroxyalkanoate, polycaprolactone, poly(lactide-co-glycolide), polycarbonate, polyamide, polyanhydride, polyamino acids, polyorthoester, polyacetate, polycyanoacrylate, degradable polyurethane, degradable polyester, or a co-polymer or blend thereof.

6. The method of claim 1, wherein the second biocompatible polymer is polylactic acid, polyglycolic acid, poly(3-hydroxybutyrate), poly(3-hydroxyvalerate), poly(3-hydroxypropionate), poly(2-hydroxybutyrate), poly(4-hydroxybutyrate), poly(4-hydroxyvalerate), poly(3-hydroxyhexanoate), poly(3-hydroxyheptanoate, poly(3-hydroxyoctanoate), poly(3-hydroxynonanoate), poly(3-hydroxytridecanoate), poly(3-hydroxytetradecanoate), poly(3-hydroxypentadecanoate), poly(3-hydroxyhexadecanoate), poly(3-hydroxyheptadecanoate), poly(3-hydroxyoctadecanoate), or a co-polymer or blend thereof.

7. The method of claim 1, wherein the first biocompatible polymer is polylactic acid.

8. The method of claim 1, wherein the inorganic material is a glass or a ceramic material.

9. The method of claim 1, wherein the inorganic material is bioactive glass, hydroxyapatite, calcium phosphate, tricalcium phosphate, or a mixture of any two or more thereof.

10. The method of claim 1, wherein a molecular weight of the first biocompatible polymer is less than 5000 g/mol and a molecular weight of the second biocompatible polymer is greater than 50,000 g/mol.

11. The method of claim 1, wherein the silane is a trialkoxysilane, a trihalosilane, or a triaminoalkylsilane.

12. The method of claim 1, wherein the allowing the primer group of the modified biocompatible polymer to react with the inorganic material comprises forming a covalent bond between the modified biocompatible polymer and the inorganic material.

13. The method of claim 1, wherein the allowing the primer group of the modified biocompatible polymer to react with the inorganic material comprises adding an acid catalyst.

14. The method of claim 1 further comprising forming the biocompatible polymer composite into a medical device.

15. The method of claim 14, wherein the medical device is a tissue scaffold or a bone scaffold.

* * * * *

UNITED STATES PATENT AND TRADEMARK OFFICE
CERTIFICATE OF CORRECTION

| | | |
|---|---|---|
| PATENT NO. | : 8,093,313 B2 | Page 1 of 1 |
| APPLICATION NO. | : 12/606771 | |
| DATED | : January 10, 2012 | |
| INVENTOR(S) | : Miller | |

It is certified that error appears in the above-identified patent and that said Letters Patent is hereby corrected as shown below:

IN THE SPECIFICATIONS:

In Column 5, Line 9, delete "polymers" and insert -- polymers. --, therefor.

In Column 9, Line 4, delete "siliane" and insert -- silane --, therefor.

In Column 10, Line 24, delete "form" and insert -- from --, therefor.

IN THE CLAIMS:

In Column 12, Line 57, in Claim 14, delete "1" and insert -- 1, --, therefor.

Signed and Sealed this
Eighth Day of May, 2012

David J. Kappos
*Director of the United States Patent and Trademark Office*